(12) United States Patent
Messina, Sr.

(10) Patent No.: US 9,693,566 B2
(45) Date of Patent: Jul. 4, 2017

(54) BROAD SPECTRUM ANIMAL REPELLENT AND METHOD

(71) Applicant: James Messina, Sr., Long Valley, NJ (US)

(72) Inventor: James Messina, Sr., Long Valley, NJ (US)

( * ) Notice: Subject to any disclaimer, the term of this patent is extended or adjusted under 35 U.S.C. 154(b) by 72 days.

(21) Appl. No.: 14/320,735

(22) Filed: Jul. 1, 2014

(65) Prior Publication Data

US 2014/0314885 A1    Oct. 23, 2014

Related U.S. Application Data

(62) Division of application No. 13/058,424, filed as application No. PCT/US2008/072993 on Aug. 13, 2008, now abandoned.

(51) Int. Cl.
 *A01N 65/06* (2009.01)
 *A01N 65/22* (2009.01)
 *A01N 65/00* (2009.01)

(52) U.S. Cl.
 CPC ............ *A01N 65/06* (2013.01); *A01N 65/00* (2013.01); *A01N 65/22* (2013.01)

(58) Field of Classification Search
 None
 See application file for complete search history.

(56) References Cited

U.S. PATENT DOCUMENTS

| | | |
|---|---|---|
| 3,009,603 A | 11/1961 | Stockdale |
| 3,980,773 A | 9/1976 | Oh et al. |
| 4,058,067 A | 11/1977 | Wright et al. |
| 4,169,902 A | 10/1979 | De Long |
| 4,388,303 A | 6/1983 | Allan |
| 4,455,304 A | 6/1984 | Yaralian |
| 4,534,163 A * | 8/1985 | Schuerch .............. D07B 1/04 57/233 |
| 4,536,583 A | 8/1985 | Mookherjee et al. |
| 4,546,858 A | 10/1985 | Nagano |
| 4,666,767 A | 5/1987 | Von Kohorn et al. |
| 4,668,294 A * | 5/1987 | Harding, Jr. ............ C09D 1/04 106/15.05 |
| 4,735,803 A | 4/1988 | Katz et al. |
| 4,783,335 A | 11/1988 | Lipshitz |
| 4,821,452 A | 4/1989 | Beckley |
| 4,849,006 A | 7/1989 | Knudson, Jr. |
| 4,965,070 A | 10/1990 | Messina |
| 4,965,204 A | 10/1990 | Civin |
| 4,971,796 A | 11/1990 | Sjogren |
| 4,983,390 A | 1/1991 | Levy |
| 5,017,377 A | 5/1991 | Sikinami et al. |
| 5,183,661 A | 2/1993 | Messina |
| D342,352 S | 12/1993 | Embrey |
| 5,368,866 A | 11/1994 | Loucas |
| 5,679,129 A | 10/1997 | Hon |
| 5,716,602 A | 2/1998 | Uick |
| 5,738,851 A | 4/1998 | Colavito |
| 5,776,478 A * | 7/1998 | Jain .................. A01N 65/00 424/405 |
| 5,783,204 A | 7/1998 | Messina |
| 5,858,384 A | 1/1999 | Levy |
| 5,885,605 A | 3/1999 | Levy |
| 5,902,596 A | 5/1999 | Levy |
| 5,942,211 A * | 8/1999 | Harper .................. A61K 8/34 424/49 |
| 6,001,874 A | 12/1999 | Veierov |
| 6,004,572 A | 12/1999 | Harvan et al. |
| 6,036,971 A | 3/2000 | Kimoto et al. |
| 6,057,266 A | 5/2000 | Colvin et al. |
| 6,083,621 A | 7/2000 | Sugimoto |
| 6,110,463 A | 8/2000 | Riggs et al. |
| 6,117,428 A | 9/2000 | Jarrett |
| 6,192,621 B1 | 2/2001 | Fain |
| 6,199,000 B1 | 3/2001 | Keller et al. |

(Continued)

FOREIGN PATENT DOCUMENTS

| | | |
|---|---|---|
| CN | 1 548 028 | 11/2004 |
| EP | 0724826 | 8/1996 |

(Continued)

OTHER PUBLICATIONS

Abdelkrim Amer, Heinz Mehlhorn. Larvicidal effects of various essential oils against Aedes, Anopheles, and Culex larvae (Diptera, Culicidae). Parasitol Res (2006) 99: 466-472.*

(Continued)

*Primary Examiner* — Frederick Krass
*Assistant Examiner* — Michael P Cohen
(74) *Attorney, Agent, or Firm* — DT Ward, PC; Donna T. Ward; Christopher P. Sullivan

(57) ABSTRACT

An animal, bird, and repellent formulation and method for warding off deer, geese, birds and insects from shrubs, grass, water, walks, parking lots in around buildings and the like. The formulation is a mixture of water, rosemary oil, mint oil, cedar oil, kaolin clay, a thickener, preservative, white distilled vinegar and dried eggs. This formulation can be applied to a support medium, such as crushed eggshells, nutshells, or corncobs and then disbursed over the surface to be protected. The mixture can also be formed into a viscous composition and sprayed over the area. Additionally, this mixture can be applied to stagnate water to kill mosquito larvae or on a variety of surfaces to repel insects such as flies, spiders, beetles, ants and so forth.

9 Claims, No Drawings

(56) References Cited

U.S. PATENT DOCUMENTS

| | | | |
|---|---|---|---|
| 6,221,649 B1 | 4/2001 | Malvar et al. | |
| 6,254,880 B1 | 7/2001 | Messina | |
| 6,266,917 B1 | 7/2001 | Hight | |
| 6,299,663 B1 | 10/2001 | Phinney | |
| 6,331,193 B1 | 12/2001 | Phinney | |
| 6,337,081 B1 | 1/2002 | Warberg | |
| 6,372,240 B1 | 4/2002 | Messina | |
| 6,383,508 B1 | 5/2002 | Messina | |
| 6,391,336 B1 | 5/2002 | Royer | |
| 6,491,949 B2 | 12/2002 | Faour et al. | |
| 6,500,463 B1 | 12/2002 | Van Lengerich | |
| 6,548,085 B1* | 4/2003 | Zobitne | A01N 65/00 424/725 |
| 6,635,266 B2 | 10/2003 | Messina | |
| 6,641,830 B1 | 11/2003 | Markham | |
| 6,641,839 B1 | 11/2003 | Geoghegan | |
| 6,645,516 B2 | 11/2003 | Auberger et al. | |
| 6,652,870 B2 | 11/2003 | Campbell et al. | |
| 6,793,937 B2 | 9/2004 | Quong | |
| 6,852,328 B1 | 2/2005 | Voris et al. | |
| 6,887,828 B2 | 5/2005 | Allen et al. | |
| 6,969,521 B1 | 11/2005 | Gonzalez et al. | |
| 7,037,515 B2 | 5/2006 | Kalafsky et al. | |
| 7,204,054 B2 | 4/2007 | Mayo et al. | |
| 7,605,096 B2 | 10/2009 | Tomarchio et al. | |
| 7,712,249 B1 | 5/2010 | Modlin et al. | |
| 7,801,489 B2 | 9/2010 | Keller | |
| 7,846,463 B2 | 12/2010 | Johal | |
| 7,858,127 B2 | 12/2010 | Overman | |
| 7,947,298 B2 | 5/2011 | La Torre | |
| 7,956,092 B2 | 6/2011 | Knoblauch et al. | |
| 8,101,657 B2 | 1/2012 | Yamada et al. | |
| 8,296,993 B2 | 10/2012 | Modlin et al. | |
| 8,404,260 B2 | 3/2013 | Reid et al. | |
| 2002/0102281 A1 | 8/2002 | Auberger | |
| 2002/0110576 A1* | 8/2002 | Messina | A01N 65/00 424/411 |
| 2003/0175369 A1 | 9/2003 | Khazan-Enache | |
| 2004/0127362 A1 | 7/2004 | Hiromoto | |
| 2004/0131627 A1 | 7/2004 | Werdyger | |
| 2005/0214337 A1* | 9/2005 | McGee | A01N 25/12 424/405 |
| 2005/0233930 A1 | 10/2005 | Cheung et al. | |
| 2006/0029630 A1* | 2/2006 | Overman | A01N 65/00 424/405 |
| 2006/0083763 A1* | 4/2006 | Neale | A01N 25/06 424/405 |
| 2006/0263326 A1 | 11/2006 | Weiser | |
| 2007/0031463 A1 | 2/2007 | Fotinos et al. | |
| 2007/0092544 A1 | 4/2007 | Mills | |
| 2007/0154504 A1* | 7/2007 | Coats | A01N 31/04 424/405 |
| 2007/0166238 A1* | 7/2007 | Duggan | A61K 9/5073 424/46 |
| 2007/0224232 A1 | 9/2007 | Sherwood | |
| 2007/0264297 A1 | 11/2007 | Scialdone et al. | |
| 2008/0020078 A1 | 1/2008 | Enan | |
| 2008/0120900 A1 | 5/2008 | O'Neal et al. | |
| 2008/0166415 A1 | 7/2008 | Markus et al. | |
| 2008/0274072 A1 | 11/2008 | Manolas et al. | |
| 2010/0040705 A1 | 2/2010 | Komai | |
| 2010/0071096 A1 | 3/2010 | Yamada | |
| 2010/0074860 A1 | 3/2010 | Kupfer et al. | |
| 2010/0104666 A1 | 4/2010 | Cox | |
| 2010/0260862 A1 | 10/2010 | Cox | |

FOREIGN PATENT DOCUMENTS

| | | | |
|---|---|---|---|
| FR | 2 576 212 | 7/1986 | |
| JP | EP 1705237 A1 * | 9/2006 | C11B 9/00 |
| WO | 9102534 | 3/1991 | |
| WO | 03013243 | 2/2003 | |
| WO | 2010019141 | 2/2010 | |
| WO | 2011142918 | 11/2011 | |
| WO | 2013/155438 | 10/2013 | |

OTHER PUBLICATIONS

Wikipedia entry for "Insect", pp. 1-5 of 31, downloaded Jun. 10, 2016, from the site: https://en.wikipedia.org/wiki/Insect.*
Definition of "rope" from Merriam Webster On-line dictionary, downloaded Jun. 10, 2016, from: http://www.merriam-webster.com/dictionary/rope.*
Definition of "ribbon" from Merriam Webster On-line dictionary, downloaded Jun. 10, 2016, from: http://www.merriam-webster.com/dictionary/ribbon.*
Burger, J. 2006. Whispers in the Pines—A Naturalist in the Northeast. Rutgers University Press. p. 206.
Database WPI 1-22, Week 199023, Thomson Scientific, London, GB; AN 1990-174630, XP002715232, & JP H02 113836 A (Mikasa Kagaku Kogyo KK) Apr. 26, 1990 (Apr. 26, 1990).
EP Office Action, App. No. EP08797777.3.
Rue, L.L 2005. Leonard Lee Rue III's Way of the Whitetail. Voyageur Press. p. 74.
Supplementary European Search Report for EP Application 08 79 7777 dated Feb. 6, 2013.
Extended European Search Report for EP Application 11 78 0980 dated Oct. 24, 2013.
Sigma-Aldrich Co. LLC catalog search results for "Thujone" 2017.
Sigma-Aldrich Co. LLC "Cedar Leaf Oil Safety Data Sheet" Version 5.4, Revision Date May 11, 2016 Print Date: Dec. 1, 2016.
United States Environmental Protection Agency "Active Ingredients Eligible for Minimum Risk Pesticide Products" updated Dec. 2015.

* cited by examiner

BROAD SPECTRUM ANIMAL REPELLENT AND METHOD

CROSS REFERENCE TO RELATED APPLICATIONS

This application is a divisional of U.S. Ser. No. 13/058,424 filed Apr. 7, 2011, entitled "Broad Spectrum Animal Repellent and Method" which is a 371 U.S. National Phase Application of International Application No. PCT/US2008/072993 filed Aug. 13, 2008, the contents of which are each incorporated herein by reference in its entirety.

BACKGROUND OF THE INVENTION

1. Field

The invention generally relates to an animal repellent and, in particular, the invention relates to such a broad spectrum repellent composition which repels a large variety of pests, is transparent and can be applied to a wide range of surfaces and to a method for the use of such a composition.

2. Prior Art

The encroachment of human habitation on heretofore rural areas has exacerbated existing problems of pest control. In recent years suburban backyards and public green spaces have been invaded by exploding deer populations, fowl who take up residence on ponds and public areas near water fouling the surface or surrounding land area. Insect pests are also more prevalent in suburban and rural areas.

Synthetic chemical controls have long been used but with increasing public awareness of health issues to humans exposed to such chemical controls has increased the need for more benign natural control measures.

In an early art deer repellent formulation and method as described in U.S. Pat. No. 4,965,070, issued Oct. 23, 1990 and U.S. Pat. No. 5,783,204 issued Jul. 21, 1998 both to the same inventor as this application, the formulation disclosed therein consisted essentially of, by volume, 68 to 90% water; 6 to 10% thiram; 0.5 to 2% chicken eggs; 1 to 2% liquid hot sauce; 2 to 16% adhesive to aid in adhering to vegetation; and 0.5 to 2% coloring dye. The dye was necessary so the coating would blend in with the foliage and not scare the pest away. There is no indication that such formulas can be used as a geese deterrent.

Related U.S. Pat. No. 5,183,661 issued Feb. 2, 1993 to the instant inventor discloses a deer repellent assembly comprising a rope support medium on which is applied a deer repellent liquid formulation consisting of, per 16 ounces of formulation, about 15 fluid ounces of water and about 0.125 ounces by weight of deshelled chicken eggs and about 0.063 ounces by weight of pepper and about 0.968 ounces by weight of seventy-five percent thiram dry and an adhesive in a quantity sufficient for adherence to the flexible rope.

An improved deer repellent formulation and method is disclosed in U.S. Pat. No. 6,254,880 issued Jul. 3, 2001 to the instant inventor comprising preparing a deer repellent formulation by admixing about 15 fluid ounces of water, about 0.125 ounces by weight of fresh chicken egg yolks, about 0.968 ounces by weight of beef animal blood and about 2 to 16% by weight of the adhesive with a dye for blending the appearance of the formulation with its environment and an adhesive for adhering the composition to a carrier.

An improved deer repellent formulation and method is disclosed in U.S. Pat. No. 6,372,240 issued Apr. 16, 2002 to the instant inventor where the formulation comprises mixing wheat flower with ground corn cobs, adding a mixture of Rosemary oil emulsion, mint oil emulsion and a thickener.

U.S. Pat. No. 5,783,204, issued Jul. 21, 1998 to the instant inventor discloses that one problem of the prior art deer repellent formulations is that, although the ingredients are common materials, they requires approval of the Environmental Protection Agency ("EPA") which involves long and costly tests. Formulations of this type are applied by small companies, such as landscape gardeners, and the obtaining of approval from the EPA is financially prohibitive. This results in widespread destruction of homeowners' landscaping because of the unfettered proliferation of deer in suburban areas. Further, the prior art materials have a limited effective life and the odor of the formulation can limit its acceptance. A further problem with the prior art compositions is that a colorant to hide their presence on the foliage is usually necessary.

U.S. Pat. No. 5,738,851 issued Apr. 14, 1998 to Colavito and U.S. Pat. No. 6,117,428 issued Sep. 12, 2000 to Jarrett avoid the EPA registration problem by utilizing, as a deer repellent, only agents derived from plants selected from the group of Amaryllidaceae consisting of *Narcissus* (common name Daffodil), *Amaryllis Belladona* (common name Naked Lady), *Crinium×Powellii* (common name Crinium Lily), *Cyrthanthus Elatus* (also known as *Vallota Purpurea*; common name Scarborough Lily), *Scadoxus* (Haemanthus) *Multiflorus* (common name Blood Lily), *Sprekelia Formosisium* (common name Jacobean Lily), *Nerine Bowdenii, Nerine Sarniensis, Eucharis Amazonica* (common name Fairy or Rain Lily), *Galanthus* (common name Snowdrops), *Chlidanthus Fragrans, Leucojum* (common name Snowflake), *Sternbergia* (common name Fall Daffodil), *Hippeastrum* (common name Amaryllis), *Hymenocallis* (common name Peruvian Daffodil), *Pamianthe Peruviana, Phaedranassa Carmioli,* and *Habranthus*.

U.S. Pat. No. 6,641,839 issued Nov. 4, 2003 to Markham discloses a deer repellent consisting essentially of 60.87% milk, 30.43% deshelled chicken eggs, 4.35% corn oil and 4.35% of a 29 percent aqueous solution of sodium lauryl sulfate, the percentages based on volume of the total composition.

More recent patents recognize the need for repellents with broader functionality.

A deer and geese repellent concentrate formulation and method is disclosed in U.S. Pat. No. 6,383,508 issued May 7, 2002 and U.S. Pat. No. 6,635,266 issued Oct. 21, 2003 both to the instant inventor where the formulation comprises of an aqueous solution or mixture containing 5 to 20 ounces of rosemary oil emulsion, 5 to 20 ounces of mint oil emulsion, 10 to 30 ounces of white distilled vinegar and 10 to 30 ounces of dried eggs, and sufficient water to make approximately one gallon of concentrate.

U.S. Pat. No. 6,337,081 issued Jan. 8, 2002 to Warberg discloses a rodent repellent composition comprising corn cob chips permeated with a volume of Canadian wilderness fragrance oil comprised of linalool 90, eucalyptus 80/85, rosemary Spanish, patchouli, turpentine rectified, caryophellene B, acetaldehyde, aldehyde C-14, fir balsam anhydrol, linalyl acetate special, dioctyl adipate, cis 3 hexenyl acetate, mousse de chene, hydroxy citronellal, iso borneol acetate, neryl acetate, fir balsam, viridine, fir needle Canadian, galaxolide 50, musk ketone, boreol leavo, hercolyn D, benzyl salicylate, camphor gum, grapefruit white, sage clary, mousse de arbre, styrallyl alcohol, vertenex, cedarwood Texas white, lemon California, veltol plus and fenchyl alcohol alpha.

U.S. Pat. No. 6,652,870 issued Nov. 25, 2003 discloses wildlife repellent comprising shellfish waste material comprising a weight percentage of the repellent in a range of 40 to 90 percent, and wherein said shellfish waste material comprises mussel material comprising soft mussel tissue in range of 20 to 40 weight percent of the shellfish waste material and ground hard mussel shell in a range of 40 to 80 weight percent of the shellfish waste material, a binder material comprising ground corn, corn oil in a range of 5 to 10 weight percent of the repellent, and colorant in a range of 0.001 to 10 weight percent of the repellent.

It is apparent that a need exists for a broad based animal pest repellent.

SUMMARY OF THE INVENTION

The instant invention comprises non-toxic animal repellent formulations suitable for use in repelling multiple species of animals and methods for the use of such compositions where the formulation comprises only natural ingredients or ingredients not requiring EPA approval.

These formulations have proved effective in repelling deer and geese, birds, insects, and for killing mosquito larvae in stagnant water.

Only natural ingredients or ingredients not requiring EPA approval are present in the composition making it useful for application by homeowners and non-licensed applicators as well as for professional use.

The formulation is a combination of components which work in combination in a synergistic manner to provide multiple layers of repulsion and which is broad spectrum in the number of animal species repelled thus avoiding the necessity of applying multiple compositions to repel various animal pests.

The formulation comprises specified amounts of plant essential oils and herb oils in an aqueous composition with sufficient optional adjuvants to promote retention of the composition on surfaces to be treated and increase effectiveness. Optional components such as dilute acids, naturally occurring insecticides, sodium chloride and potassium soaps increase the range of activity of the base composition with regard to the number of animal species repelled and the duration of repulsion effect. Potassium sorbate may be used as a preservative.

The improved broad spectrum animal repellent formulations are suitable for application to varied surfaces such as structural surfaces, vegetation, soil and bodies of water.

Existing products have a limited spectrum of repellency requiring the use of multiple formulations to prevent encroachment of animal pests.

Therefore it is an object of the present invention is to provide an improved animal repellent formulation for application to plants, grass, water, walks, parking lots in and around buildings, and the like, which can be acceptable under EPA regulations.

Another object of the invention is to provide an animal repellent formulation more acceptable to humans.

Another object of the invention is to make use of EPA-approved components without reduction of the effectiveness of the treatment.

A still further object is to provide such a composition which is transparent.

Other objects and the advantages of the invention will appear from the following description.

DETAILED DESCRIPTION

The present invention provides an improved broad spectrum animal repellent formulation which does not require EPA approval.

The formulation comprises specified amounts of plant essential oils and herb oils in an aqueous composition with sufficient optional adjuvants to promote retention of the composition on surfaces to be treated and increase effectiveness. The formulation is preferably an aqueous solution or mixture, consisting of water and a composition containing rosemary oil, cedar oil, mint oil, xanthan gum as a thickener and water. The optional addition of white distilled vinegar, dried eggs and table salt can usefully modify the formulation. A preservative, such as potassium sorbate can be added to the formulation.

The formulation may be a concentrate of the active components to be diluted with water at the time of use or it may be in ready-to-use form with the components at the proper concentration. The compositions are typically prepared as a concentrate and diluted to application strength when used.

The formulation comprises specified amounts of components consisting of plant essential oils and herb oils in an aqueous composition with sufficient adjuvant to promote retention of the composition on surfaces to be treated. The active components interact to function in a synergistic manner to provide multiple layers of repulsion. The repulsive effect is broad spectrum with regard to the number of animal species repelled thus avoiding the necessity of applying multiple compositions to repel various animal pests.

The necessary components of the composition include an essential oil and an herb oil Among the preferred essential oils are eucalyptus oil and cedar oil, with cedar oil being most preferred. Among the preferred herb oils are mint and rosemary oils with rosemary oil being most preferred. Cinnamon oil can be substituted but is not preferred.

Formulation

The concentrated formulation is an aqueous solution or mixture, comprising a composition of multiple components that may be adjusted either in the preparation of the concentrate or during the final dilution step prior to application. The large animal formulation differs from the insect formula in that several components of the large animal formulation are not present in the insect formulation. Table 1 shows the amounts of the various components.

This Table 1 represents the range of the amount of each component (in % by weight) in the concentrate for formulations useful for repelling large animals and Table 2 represents the range of the amount of components (in % by weight) useful for repelling insects.

TABLE 1

| | Animal [Deer & Goose] | | |
|---|---|---|---|
| Component | Acceptable | Preferred | Most Preferred |
| Rosemary oil | 0.05-8.5 | 2-7 | 1-4.5 |
| Mint oil | 0.05-8.5 | 2-7 | 1-4.5 |
| Cedar oil | 0.05-29 | 5-20 | 1-8.0 |
| Clay | 0.07-10 | 0.1-8 | 1.2-5 |
| P sorbate | 0.01-1 | 0.03-0.75 | 0.04-0.1 |
| Zanthan Gum | 0.02-1.25 | 0.03-1.0 | 0.04-.75 |
| Egg White | 0.15-15 | 0.2-10 | 0.25-7 |
| Salt | 0.03-2 | 0.1-1.5 | 0.3-1 |
| Vinegar | 0.01-7 | 0.05-5 | 0.1-3 |
| Water | 0.10-99.6 | 15-85 | 25-80 |

TABLE 2

| | Insect | | |
|---|---|---|---|
| Component | Acceptable | Preferred | Most Preferred |
| Rosemary oil | 0.07-8.5 | 0.02-7 | 0.1-4 |
| Mint oil | 0.07-8.5 | 0.02-7 | 0.1-4 |
| Cedar oil | 2.5-40 | 9-32 | 15-30 |
| Clay | 1.0-9.3 | 2-7.0 | 3.0-6.0 |
| P sorbate | 0.01-1.0 | 0.03-0.75 | 0.04-0.1 |
| Zanthan Gum | 0.02-1.25 | 0.03-1.0 | 0.04-0.75 |
| Egg White | N/A | N/A | N/A |
| Salt | N/A | N/A | N/A |
| Vinegar | N/A | N/A | N/A |
| Water | 20-90 | 25-85 | 26-80 |

Prior to use the concentrate is diluted with water per part of concentrate as disclosed in the following Table.

| | Animal [Deer & Goose] | | |
|---|---|---|---|
| Component | Acceptable | Preferred | Most Preferred |
| Water per part Concentrate | 2-34 | 5-25 | 6-12 |

| | Insect | | |
|---|---|---|---|
| Component | Acceptable | Preferred | Most Preferred |
| Water per part Concentrate | 3-25 | 5-17 | 6-15 |

A thickener, such as xanthan gum or the like, can be added to keep the ingredients in suspension in the water.

Also, a preservative, such as potassium sorbate can be added to the formulation. Typical would be 0.03 to 3% of preservative.

The addition of cedar oil to the composition enhances the effectiveness of the composition. It also adds ability to repel insects and kill mosquito larvae in water.

Prior to application to plants, grass, water, walks, parking lots, in and around buildings, and the like, the composition is diluted at the time of use for repelling large animals to one part of repellent to approximately 2 to 34 parts water, preferably 5 to 25 parts water, most preferably 6 to 12 parts water. The mixture is stirred until a uniform composition is obtained.

In certain instances, when weather conditions are dry, a preservative such as potassium sorbate can be used. A thickener can be added to give the composition the desired application characteristics. Typical would be 1 to 5% of the total composition of thickener.

All of the percentages are by weight of the composition.

Cedarwood Oil

A particularly preferred essential oil is cedar or cedarwood oil. Although termed cedarwood oils, the most important oils of this group are produced from distilling wood of a number of different junipers/cypresses (*Juniperus* and *Cupressus* spp.), rather than true cedars (*Cedrus* spp.).

The commonly used cedarwood oils contain a group of chemically related compounds, the relative proportions of these depending on the plant species from which the oil is obtained. These oils contain varying amounts of cedrol and cedrene.

Cedarwood oil is known and used as an personal insect repellent for spraying on exposed skin. Compositions containing 1% cedar oil and 99% essence of *Juniperus virginiana* are known as an inset repellant for human use sprayed on areas of skin exposed to insects. Cedar oil repels mosquitoes, flies, fleas, chiggers, no-see-ums and numerous other insects.

Herb Oils

An essential oil is any concentrated, hydrophobic liquid containing volatile aroma compounds from plants. They are also known as volatile or ethereal oils, or simply as the "oil of" the plant material from which they were extracted, such as oil of clove. The term essential indicates that the oil carries distinctive scent (essence) of the plant.

Essential oils are typically extracted by distillation. Other processes include expression and solvent extraction.

Camphor is a waxy, white or transparent solid with a strong, aromatic odor. It is a terpenoid with the chemical formula $C_{10}H_{16}O$. It is found in wood of the camphor laurel (*Cinnamomum camphora*), a large evergreen tree found in Asia (particularly in Borneo and Taiwan). It also occurs in some other related trees in the laurel family, notably *Ocotea usambarensis*.

*Mentha* (mint) is a genus of about 25 species (and many hundreds of varieties of flowering plants in the family Lamiaceae (Mint Family). Species within *Mentha* have a subcosmopolitan distribution across Europe, Africa, Asia, Australia, and North America. Several mint hybrids commonly occur.

The most common and popular mints for cultivation are peppermint (*Mentha×piperita*), spearmint (*Mentha spicata*).

Mint essential oil and menthol are extensively used as flavorings in breath fresheners. The substances that give the mints their characteristic aromas and flavors are menthol and pulegone.

Mint oil is known as an insecticide for its ability to kill some common pests like wasps, hornets, ants and cockroaches.

The duration and scope of effectiveness of the formulation may be increased by adding eucalyptus oil, citronella, soybean oil, neem oil, and/or Deet.

The duration and scope of effectiveness is also increased by adding a dilute acid to the composition, especially acetic acid, which may be in the form of vinegar, preferably white distilled vinegar having an acid content of between 3.5 and 5% acetic acid.

Insecticide—Pyrithrin

An additional optional component is a natural insecticide such pyrithrin. The pyrethrins are a pair of natural organic compounds that have potent insecticidal activity. Pyrethrin I and pyrethrin II are structurally related esters with a cyclopropane core. They differ by the oxidation state of one carbon and exist as viscous liquids.

The pyrethrins are contained in the seed cases of the perennial plant pyrethrum (*Chrysanthemum cinerariaefolium*), which is grown commercially to supply the insecticide. Pyrethrins are neurotoxins that attack the nervous systems of all insects.

When present in amounts not fatal to insects as in the present formulations, they appear to have an insect repellent effect. They are harmful to fish, but are far less toxic to mammals and birds than many synthetic insecticides. They are non-persistent, biodegradable, break down easily on exposure to light or oxygen and are considered to be among the safest insecticides for use around food.

Among the synthetic analogs of pyrithrin is permethrin, widely used as an insecticide and acaricide and as an insect repellent. It is a member of the pyrethroid family and functions as a neurotoxin, by prolonging sodium channel activation and is the preferred synthetic pyrethroid although other members may be utilized in the present invention.

Optional Components

Further optional components include sodium chloride and potassium soaps.

Depending on the components of the formulation, it is desirable to add a preservative such a potassium sorbate.

Optional components such as dilute acid, other naturally occurring insecticides, sodium chloride and potassium soaps increase the range of activity of the base composition with regard to the number of animal species repelled and the duration of repulsion effect.

Water should not be applied to the treated area for at least 20 minutes after application.

Adjuvants

The following brief descriptions of some of the categories of adjuvants may be helpful in clarifying the many functions adjuvants can perform: wetter-spreaders, stickers, foam retardants, buffers, acidifiers.

A spray drop must be able to wet the surface and spread out or cover an area to perform its control function. In some situations, additional adjuvant is needed for good coverage. The surfactant reduces the surface tension of the water on the surface of the spray drop and by reducing the interfacial tension between the spray drop and surface. This requires a surfactant that will preferentially aggregate at these surfaces.

A sticker can perform three types of functions. It can increase the adhesion or "stickiness" of solid particles that otherwise might be easily dislodged from a leaf surface, sort of glue them on as it were. It can also reduce evaporation of the formulation. The third function can be to provide a waterproof coating. If the sticker is not water soluble, it can provide a degree of protection from this form of loss.

Many of the stickers contain surfactants as their principal functioning agent and give both a sticker action and a wetter-spreader action. These will perform the first two functions quite well. But since the surfactants that provide wetter-spreader action must be somewhat water soluble, they may not provide good protection from rain. This will be provided by products that contain natural resins (rosin), or other waterproofing agents.

Some formulations will create foam in spray tanks as a result of both the surfactants used in the concentrate formulation and the type of spray tank agitation. This foam can be reduced or eliminated by a small amount of foam inhibitor.

Some water used for diluting formulations is alkaline (high pH). If the pH is sufficiently high and the pesticide is subject to degradation by alkaline hydrolysis, it may be necessary to lower the pH of the mix water to a pH in the range of 3 to 7, preferably 3.75 to 4.25.

Buffers

Buffers containing phosphoric acid or a salt of phosphoric acid, will lower the pH of the water and tend to stabilize the pH at an acceptable value. The efficacy of the buffer depends on its concentration of phosphoric acid and the degree of alkalinity or "hardness" of the mixing water that is being neutralized. The more alkaline the water, the greater the amount of buffer that will be required.

Some buffers have sufficient surfactant present to also perform as wetter-spreaders. The concentration of surfactant and phosphoric acid are usually lumped together and it is not possible to determine the concentration of either and thus predict their efficacy. It appears that a useful range for phosphoric acid buffer concentration is from about 2 to 10%.

Buffers that acidify alkaline spray waters increase the effectiveness. Buffers can help increase the residual life of the formulation about two-fold and can result in reducing the number of spray applications per season. Muriatic acid, Buffer-X or vinegar are not effective for this purpose.

Sticker-spreaders can be made of many different components, organic or inorganic. Some are silicone-based surfactants, oils, emulsifiers and buffering agents, while others may contain combinations such as fish oil or fatty acid soaps or emulsified soybean oil.

Concentrated multipurpose wetting agents typically contain a blend of bio-degradable, non-ionic surfactants and an emulsified silicone type anti-foam preparation. This action provides uniform wetting and coverage.

The use of these adjuvants provides varied benefits including improved coverage of the spray both in the soil and on plant surfaces, increased retention on surfaces, reduced evaporation, reduced foaming problems in the tank, easier sprayer cleaning and lubrication of pump and sprayer nozzles.

Application

The compositions may be applied by any convenient method although it is expected that spraying will be the application method of choice in most circumstances. Where longer lasting effects are desired a thicker version of the composition may be brushed or otherwise coated onto a surface.

Since the method of application is variable, the amount of the composition applied depends on the operator and the dilution and whether it is being utilized to repel large animals or insects. However, a typical application technique would apply one gallon of the diluted concentrate per 4,000 square feet of surface area in a fine spray.

As an alternate procedure, the composition can be impregnated into crushed eggshells, nutshells or corncobs, wood chips or other particulate substrates and spread evenly over the area to be protected. The particle size of these materials can range in size. Typically 1 to 3 ounces of concentrated formula is used to wet 1 pound of granular material. Once dry, the granular product can be applied to 1000 square feet of surface area.

In another embodiment, the composition can be left in containers which are distributed in a uniform manner around the area being treated.

As an alternate procedure, the composition can be impregnated into or coated onto a surface to be protected. In this embodiment, a thickener or thixotropic agent is added to the composition.

Various types of solid materials may be protected by the disclosed compositions. Plant material, including woody plants may be protected from browsing animals. Plant material including grasses, may be sprayed to prevent insects from alighting on the plant.

Exterior surfaces of buildings, walls, concrete and asphalt and other solid non-living surfaces may be sprayed to prevent animals from alighting on such surfaces.

The formulation may be applied to clothing or other fabric or sheet goods to prevent insects from alighting on the material or biting through the material. The fabric may be permeable or impermeable and may be woven or non-woven. Examples of materials to which the compositions may be applied are cottons and other natural fibers or synthetic fibers or sheet goods such as nylon, polyester or polypropylene. If the material is permeable the composition may be absorbed; if impermeable the composition will act as a coating on the surface of the fiber or sheet goods.

In one embodiment the compositions are applied to ribbon substrates of various types.

The compositions are useful for coating tents and mosquito netting.

The formulation may be applied to the skin, fur or pelt of pets and domestic or other animals to minimize insect problems. Use of the composition on the surface of various farm structures, particularly on surfaces inside barns where animals are kept or milked will minimize insect interference with farm operations and animals.

The formulation may also be applied to the skin of humans, preferably by spraying.

One important use of the formulations is the application of the formulation to the surface of bodies of stagnant water. The formulations are effective to prevent the growth of mosquito larvae and the larvae of other insects.

The following examples are given for purposes of illustration and not by way of limitation. The following examples are given for purposes of illustration and not by way of limitation.

Example 1

An animal repellent formulation concentrate for outdoor application is prepared by mixing together 2.5 ounces of rosemary oil, 2.5 ounces of mint oil and 7.75 ounces cedar oil. Water is added to make 128 ounces of concentrate. The concentrate is diluted with water at a 1 to 9 ratio and applied to plant foliage in a fine mist from a power spray.

Example 2

The following are added to the animal repellent formulation of Example 1:
2.5 ounces of white distilled vinegar;
0.5 ounces of salt;
4 ounces of dried chicken eggs.

Example 3

The repellent formulation of Example 1 is mixed with potassium sorbate preservative in an amount of 0.05 weight % to preserve the formulation.

Example 4

The quantity of repellent formulation of Example 2 is mixed with 0.5 ounce Zanthan gum as a thickener.

Example 5

The repellent formulation of Example 2 is mixed with 2 ounces of kaolin clay powder per gallon of concentrate formulation, to act as a sticker, to aid in the adherence of the formulation to the surface to be treated.

Example 6-8

A solid formulation of the animal repellent formulation of Example 2 is formed by admixing 1 pound of crushed eggshells or granular corncob or crushed nutshells, respectively with 4 fluid ounces of the animal repellent formulation of Example 2, drying the repellant particle and evenly distributing the repellant over the area to be protected.

Example 9-11

A solid formulation of the animal repellent formulation of Example 1 is prepared by mixing one pound by weight of crushed eggshells, nutshells, or corncobs granules, respectively, in a particle size distribution from dustless fine particles to about one-quarter inch overall thickness particles with 7.5 fluid ounces of the animal repellent formulation of Example 1 drying the repellant particles and evenly distributing the repellant over the area to be protected.

While the invention has been described in its preferred embodiments, it is to be understood that the words which have been used are words of description rather than limitation, and that changes may be made within the purview of the appended claims without departing from the true scope and spirit of the invention in its broader aspects.

What is claimed is:

1. A method of repelling animals comprising:
   (a) preparing an aqueous animal repellent comprising:
      from about 0.004 to about 1 weight percent rosemary oil,
      from about 0.004 to about 1 weight percent mint oil,
      from about 0.004 to 4 weight percent cedar oil,
      from about 0.005 to about 1 weight percent clay, and
      optionally comprising one or more adjuvants, wherein said one or more adjuvants are selected from potassium sorbate, xanthan gum, dried eggs, salt, and vinegar;
   (b) applying the aqueous animal repellent to a substrate, wherein said substrate is a ribbon; and
   (c) repelling animals with said ribbon.

2. The method of claim 1, wherein the one or more adjuvants comprise:
   from about 0.002 to about 0.2 weight percent xanthan gum,
   from about 0.002 to about 0.3 weight percent salt, and
   from about 0.0008 to about 1 weight percent vinegar.

3. The method of claim 2, wherein the aqueous animal repellent comprises dried eggs.

4. The method of claim 2, wherein the one or more adjuvants comprise 0.05 weight percent potassium sorbate.

5. The method of claim 1, wherein said animals are selected from the group consisting of mammals and birds.

6. The method of claim 1, wherein the aqueous animal repellent is prepared using a mix water, wherein the pH of the mix water is first adjusted to a pH of from pH 3 to pH 7.

7. The method of claim 6, wherein the pH of the mix water is adjusted with phosphoric acid or a salt of phosphoric acid.

8. The method of claim 1, wherein the ribbon comprises a permeable fabric.

9. The method of claim 8, wherein the permeable fabric comprises a synthetic fiber.

* * * * *